United States Patent
Smith (10) Patent No.: US 7,775,370 B2
(45) Date of Patent: Aug. 17, 2010

(54) PARTICLE SORTING BY FLUIDIC VECTORING

(75) Inventor: Barton L. Smith, Logan, UT (US)

(73) Assignee: Utah State University, North Logan, UT (US)

( * ) Notice: Subject to any disclaimer, the term of this patent is extended or adjusted under 35 U.S.C. 154(b) by 955 days.

(21) Appl. No.: 11/385,406

(22) Filed: Mar. 21, 2006

(65) Prior Publication Data

US 2006/0207918 A1  Sep. 21, 2006

Related U.S. Application Data

(60) Provisional application No. 60/663,813, filed on Mar. 21, 2005.

(51) Int. Cl.
*B03B 5/00* (2006.01)
(52) U.S. Cl. .................... 209/156; 209/133; 209/139.1; 209/142; 209/722
(58) Field of Classification Search ......... 209/155–157, 209/160, 208, 209
See application file for complete search history.

(56) References Cited

U.S. PATENT DOCUMENTS

| | | | | |
|---|---|---|---|---|
| 2,616,563 A | * | 11/1952 | Hebb | 209/722 |
| 3,498,453 A | * | 3/1970 | Zielina | 209/133 |
| 3,739,893 A | * | 6/1973 | Kaufmann | 193/17 |
| 3,825,116 A | | 7/1974 | Greenwood | |
| 3,836,085 A | * | 9/1974 | Brown | 241/19 |
| 4,175,662 A | * | 11/1979 | Zold | 209/552 |
| 4,279,624 A | * | 7/1981 | Wilson | 95/269 |
| 4,292,050 A | * | 9/1981 | Linhardt et al. | 95/269 |
| 4,699,114 A | | 10/1987 | Giannotti | |
| 4,747,939 A | | 5/1988 | Kampe | |
| 4,853,112 A | * | 8/1989 | Brown | 209/142 |
| 4,863,491 A | | 9/1989 | Brandt et al. | |
| 5,407,079 A | * | 4/1995 | Rancourt | 209/23 |
| 5,715,946 A | * | 2/1998 | Reichenbach | 209/156 |
| 6,206,202 B1 | | 3/2001 | Galk et al. | |
| 6,213,307 B1 | * | 4/2001 | Stein | 209/139.1 |
| 6,454,945 B1 | * | 9/2002 | Weigl et al. | 210/634 |

(Continued)

FOREIGN PATENT DOCUMENTS

EP      0693958 B1    1/1998

OTHER PUBLICATIONS

Office Action mailed Oct. 14, 2008 in U.S. Appl. No. 11/756,213, filed May 31, 2007.

(Continued)

*Primary Examiner*—Patrick Mackey
*Assistant Examiner*—Terrell H Matthews (57) ABSTRACT

Disclosed are embodiments of apparatus and methods for separating particles in a fluid stream by size. In one illustrative embodiment of an apparatus for separating such particles, a housing is provided, which defines a channel for a fluid stream containing particles. A suction channel is provided, which terminates at a suction port. The suction port is positioned adjacent to the fluid stream. A blowing channel terminating at a blowing port is also provided. The blowing port is positioned adjacent to the suction port such that the suction port is positioned in between the fluid stream and the blowing port. The blowing port and the suction port are configured to create a low pressure region and thereby redirect the first fluid stream towards the low pressure region.

8 Claims, 6 Drawing Sheets

U.S. PATENT DOCUMENTS

| | | | | |
|---|---|---|---|---|
| 6,631,808 | B2 * | 10/2003 | Sparks | 209/33 |
| 6,827,911 | B1 * | 12/2004 | Gering | 422/186.3 |
| 7,150,812 | B2 * | 12/2006 | Huang et al. | 204/451 |
| 7,157,274 | B2 * | 1/2007 | Bohm et al. | 435/325 |
| 7,276,170 | B2 * | 10/2007 | Oakey et al. | 210/767 |
| 7,402,131 | B2 * | 7/2008 | Mueth et al. | 494/36 |
| 2002/0179499 | A1 | 12/2002 | Kenning et al. | |
| 2003/0186228 | A1 | 10/2003 | McDevitt et al. | |
| 2003/0221996 | A1 * | 12/2003 | Svoronos et al. | 209/1 |
| 2006/0118479 | A1 * | 6/2006 | Shevkoplyas et al. | 210/433.1 |

OTHER PUBLICATIONS

Barton L. Smith, "Aerodynamic Vectoring Particle Sorting," Proceedings of ASME-FED 2006, 2006 ASME Fluids Engineering Summer Conference Miami, USA, Jul. 17-20, 2006, Copyright 2006 by ASME, pp. 1-6, Utah State University (FEDSM2006-98266).

Barton L. Smith, "Particle Size Classification Through Aerodynamic Jet Vectoring," Proceeding of HT-FED 2007, 2007 ASME Fluids Engineering Summer Conference, San Diego, USA, Jul. 30-Aug. 2, 2007, Copyright 2007 by ASME, Utah State University (HT-FED2007-37267).

Office Action mailed Apr. 1, 2008 in U.S. Appl. No. 11/756,213, filed May 31, 2007.

Shibin Liang, "Numerical Study of Classification of Ultrafine Particles in a Gas-Solid Field of Elbow-Jet Classifier," Proceedings of FESM2006, 2005 ASME Fluids Engineering Division Summer Meeting and Exhibition, Jun. 19-23, 2005, pp. 1-9, Houston, TX.

"Sieve/Classfier," Matsubo Classification Elbow-Jet, http://www.matsubo-funtai.com/english/en_details/en_e02.htm, Matsubo Corporation, 2002, 2 pgs.

Notice of Allowance mailed February 25, 2009 in U.S. Appl. No. 11/756,213, filed May 31, 2007.

* cited by examiner

PARTICLE SORTING BY FLUIDIC VECTORING

RELATED APPLICATIONS

This application claims the benefit under 35 U.S.C. §119 (e) of U.S. Provisional Patent Application No. 60/663,813, filed Mar. 21, 2005, and titled "Particle Sorting by Fluidic Vectoring," which is incorporated herein by specific reference.

TECHNICAL FIELD

The present invention relates generally but not exclusively to sorting particles in a fluid stream.

BRIEF DESCRIPTION OF THE DRAWINGS

Understanding that drawings depict only certain preferred embodiments of the invention and are therefore not to be considered limiting of its scope, the preferred embodiments will be described and explained with additional specificity and detail through the use of the accompanying drawings in which.

DETAILED DESCRIPTION OF PREFERRED EMBODIMENTS

In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments.

Disclosed are embodiments of apparatus and methods for separating particles in a fluid stream by size. In one embodiment, as a fluid jet is turned or redirected—i.e., aerodynamically vectored—particles present in the jet flow experience a resultant force based largely upon their size and due to the counteracting effects of pressure and drag on the particles inertial tendencies. Larger particles will tend to remain on straighter paths and, thus, can be segregated from smaller particles that tend to more closely follow the vectored jet flow. In such embodiments, a wide range of particle sizes may be separated with a single device (i.e., single stage) and a small pressure drop. This separation may occur without contact between the particles and surfaces of the separation device. Aerodynamic vectoring may also allow for collectors of sorted particles to be designed to collect many different particle sizes across the continuum of sizes present in the sample. The particle sorting methods and devices described herein may be utilized at a wide range of scales and may be used in conjunction with liquids as well as gases.

In an illustrative method, a first fluid stream or jet is provided having particles disposed therein. A port is provided for the first fluid stream. A second fluid stream is also provided, along with a port for the second fluid stream adjacent to the first fluid stream port. A low pressure region is created adjacent to the first fluid stream so as to redirect the first fluid stream towards the low pressure region. A third fluid stream may also be provided, along with a port for the third fluid stream. The third fluid stream port may be positioned adjacent to the second fluid stream port such that the second fluid stream port is positioned in between the first and third fluid stream ports. In a preferred implementation, the second fluid stream is a suction stream and the third fluid stream is a blowing stream.

In an illustrative apparatus, a housing is provided defining a channel for a fluid stream containing particles. A suction channel is provided, which terminates at a suction port. The suction port is positioned adjacent to the fluid stream. A blowing channel terminating at a blowing port is also provided. The blowing port is positioned adjacent to the suction port such that the suction port is positioned in between the fluid stream and the blowing port. The blowing port and the suction port are configured to create a low pressure region and thereby redirect the first fluid stream towards the low pressure region.

An illustrative embodiment of an apparatus for particle sorting via aerodynamic jet vectoring is depicted in FIG. 1. The embodiment of FIG. 1 includes a channel 10 directing a fluid stream 20. Fluid stream 20 includes particles 22. Particles 22 may have a variety of sizes, which, as set forth in greater detail below, will determine the ultimate trajectory of the particles 22 in fluid stream 20. A fluid stream port 25 is provided, at which fluid stream 20 exits from channel 10. A blowing port 30 is also provided, which directs a blowing fluid stream 35 therethrough. Likewise, a suction port 40 is provided, which directs a suction fluid stream 45 therethrough. The blowing and suction fluid streams may be comprised of air, or of any other gas or liquid as desired.

A low-pressure region 50, indicated generally by the dashed circle in FIG. 1, is generated by suction fluid stream 45 exiting suction port 40 adjacent to the exit of fluid stream 20. The low-pressure region 50 is further maintained by blowing fluid stream 35 exiting blowing port 30 adjacent to suction port 40.

As illustrated in the embodiment of FIG. 1, aerodynamic vectoring involves applying secondary flows near the exit plane of a fluid stream or jet, thereby resulting in redirection of the flow upstream of the exit or port. In the embodiment of FIG. 1, steady blowing is provided through a first port near the jet port and steady suction is provided through a second port near the jet port.

Figure 1:
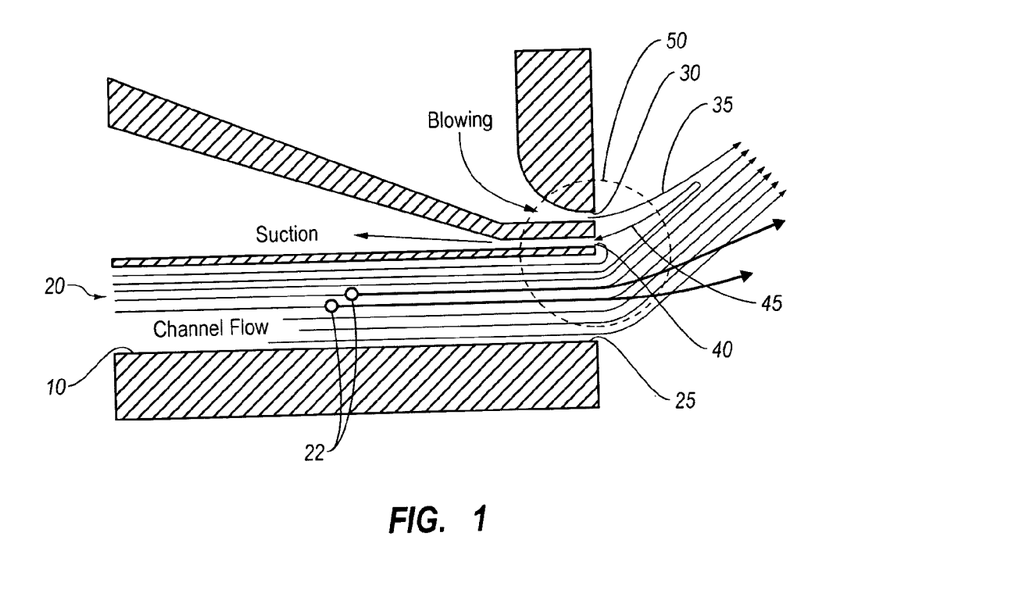
FIG. 1 is a cross-sectional view of one embodiment of an apparatus for separating particles in a fluid stream.

In the embodiment shown in FIG. 1, suction flow is applied immediately adjacent to the port of the jet in between the jet and the blowing flow. The blowing and suction ports/flows in this embodiment function together to create a low-pressure re-circulation region 50 above the jet 20. This arrangement may be configured to prevent ambient fluid from being drawn into the suction port 40 and instead drawing the fluid from the primary jet 20 through the suction port 40. The low pressure region 50 results in the jet 20 turning or being redirected toward the low pressure region 50. Aerodynamic vectoring may decrease the pressure drop across the flow channel 10 due to the presence of the low pressure region 50 near the exit 25. It has been found that the flow rate through the channel tends to increase when a vectored jet is employed with the blower at a constant speed.

Figure 2:
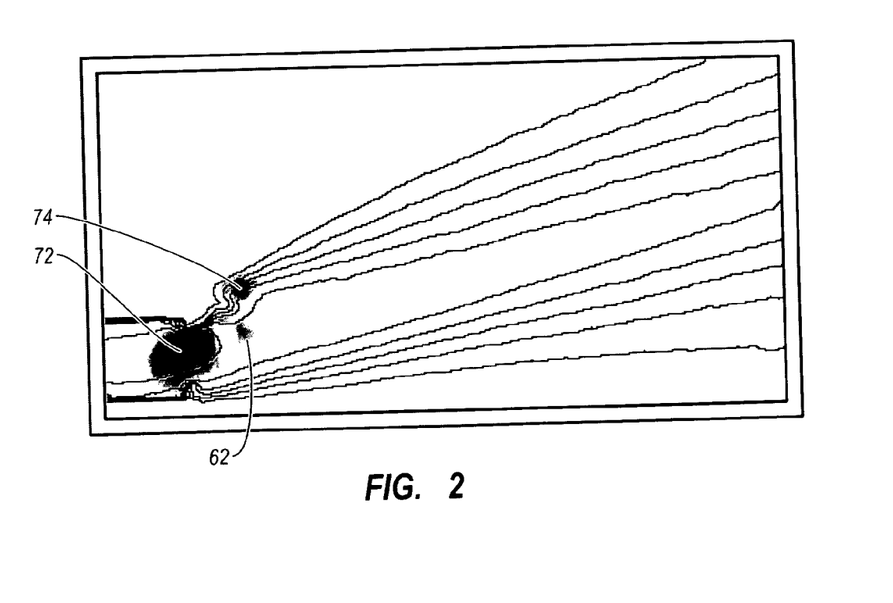
FIG. 2 illustrates a vertical pressure gradient field, generated by an apparatus for separating particles in a fluid stream, with contour lines of constant velocity superimposed thereon.
Figure 5:
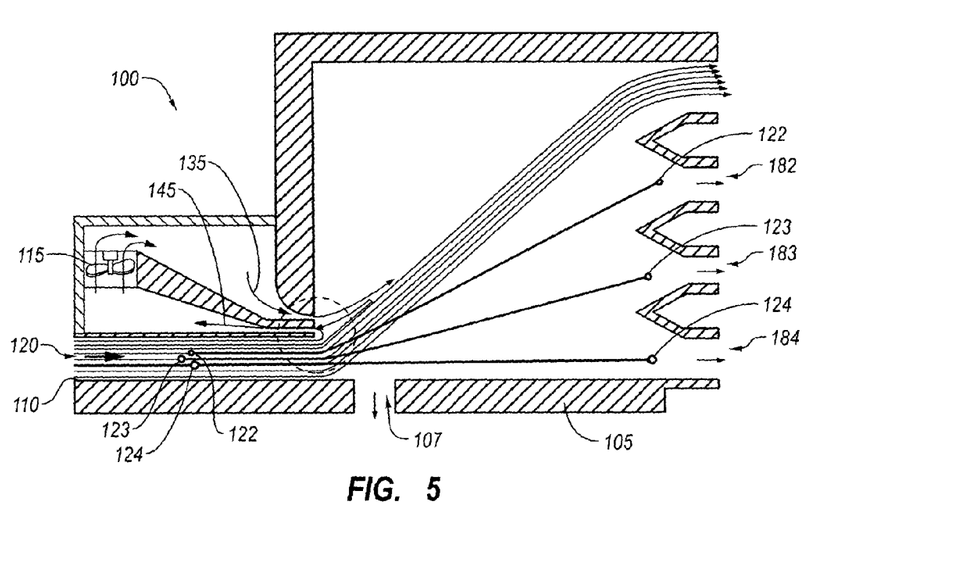
FIG. 5 is a cross-sectional view of another embodiment of an apparatus for separating particles in a fluid stream.

As described above, it is thought that aerodynamic vectoring occurs due to a low-pressure region formed along the upper surface of the flow channel near the exit of the jet. The vertical pressure gradient field, $\partial P/\partial y$, for a typical vectored flow is shown in FIG. 2. FIG. 2 illustrates a vertical pressure gradient field with contour lines of constant velocity superimposed. A particle located in region 62 will encounter a downward pressure force, while a particle in region 72 or region 74 will experience an upward force. In addition to vectoring the flow, this pressure field can be used to modify the trajectory of particles within the flow. A negative pressure gradient (regions 72 and 74) indicates that the pressure below a particle is more than above, and that a particle in such a region location will experience an upward force. A positive pressure gradient (region 62) indicates the opposite, such that particles located there will experience a downward force. Other embodiments may be configured such that only region 72 near the exit plane of the jet channel would be present. Possible means to eliminate the pressure gradients downstream of the blowing port are discussed infra.

When the jet flow contains particulate, each particle in the flow will experience several forces, including aerodynamic forces (i.e., pressure P), added mass M, drag D, and buoyancy B. The effect of each of these forces is accounted for in the following particle equation of motion:

$$m_p \frac{dV_i}{dt} = P_i + M_i + D_i + B_i$$

with $$P_i = m_f \left[ \frac{Du_i}{Dt} - \nu \nabla^2 u_i \right]_{Y(t)}$$

$$M_i = -\frac{m_F}{2} \frac{d}{dt} \{V_i(t) - u_i[Y(t), t]\}$$

$$D_i = -6\pi a \mu (V_i(t) - u_i[Y(t), t])$$

$$B_i = (m_p - m_F) g_i$$

The particle in this equation is of radius a and mass $m_p$, is located at Y(t), and moves with velocity V(t). The term on the left-hand side of the first equation present above is the particle inertia, which is balanced by the four forces on the right. In this two-dimensional flow, i=1, 2 . . . refers to the streamwise x and cross-stream y directions, respectively. The fluid is of kinematic viscosity ν and dynamic viscosity μ. The mass of the fluid displaced by the particle is $m_F$. The fluid velocity field u must be known to solve for the particle path.

As those having ordinary skill in the art will appreciate, larger particles experience larger pressure, drag, and buoyancy forces, while heavier particles have more inertia. By turning or redirecting the fluid flow, the relative magnitudes of these forces will differ for varying particle parameters, such as mass, density and/or volume/diameter. Since the balance of these forces determines the final trajectory of the particle, turning the flow leads to a physical separation of particles of different sizes. Particles of a desired size can then be collected downstream in one or more particle collectors or other collection areas/structures. It should be understood that the term "size", as used herein, may refer to a single parameter, or a combination of parameters, that affect the trajectory of a particle within a fluid stream, such as mass, density, or volume/diameter.

A wide variety of blowing and suction combinations may be used in accordance with the principles of the invention to produce various alternative configurations. As previously mentioned, a wide variety of fluids, whether liquids or gases, may also be used. The equation of motion identified above may be solved to predict the trajectory of a particle of any size and/or density. It should be understood, however, that the drag term may require modification under certain situations (e.g., when the particle is small compared to the mean free path of the fluid).

To illustrate, FIG. 3 shows the predicted trajectory of water droplets released upstream of the exit of the jet at the same location (the center of the channel). The diameter of each particle in micrometers is indicated on the figure next to each predicted trajectory. The jet exit or port in the graph is at x=0. The results show that, for a given jet speed, particles of, for example, a density of 1000 times that of air in the range 1-40 μm in diameter can be effectively sorted. At higher jet speeds, this range may increase.

As shown in FIG. 3, particles of a sufficiently small size, or of a density similar to the fluid in which they move, will tend to follow the jet flow. However, the more massive the particle, the more likely it is to remain on a relatively straight path, even as the jet flow turns. Thus, deliberately redirecting or causing the flow to turn can result in a particle response that is dependent on its size.

FIG. 4 is a graph showing experimentally measured trajectory angles (θ) as a function of droplet diameter (in μm). The graph demonstrates the correlation between the size of a particle in a fluid stream and the degree to which the particle is redirected through the vectoring methods described herein.

One particular embodiment of an aerodynamic vectoring particle sorter 100 is shown in FIG. 5 (not to scale). Particle sorter 100 includes a housing 105, which may be used to reduce or eliminate external influences on pressures within the device. A particle-laden stream 120 enters from the left and travels through channel 110. The suction and blowing flows in this embodiment are both provided by a single high-pressure blower 115. Particles of a variety of sizes may be included within the stream 120. To illustrate, FIG. 4 shows three different particles—particles 122, 123, and 124—ranging in size (with their relative sizes exaggerated) from small to large, respectively. Particles small enough to follow the vectored flow leave with the exhaust at the top, while larger particles are collected through one or more output ports and into collectors according to their size on the right. Thus, particle 122 is shown following a trajectory that leads it into collection port 182, particle 123 is shown following a trajectory that leads to collection port 183, and particle 124 is shown following a trajectory that leads to collection port 184.

A vent, such as vent 107, may be provided to prevent the jet flow from attaching to the lower wall of the device. Multiple output ports/bins at different locations may also be used to collect particles of various sizes. Although three collection ports are shown in FIG. 5, any number of collection ports greater than, or less than, three may be used. Two ports may be useful in some configurations designed for separating or removing particles of a minimum (or maximum) size, mass, or other parameter. More than three ports may be desirable in other configurations, with the maximum number of collection points being limited only by installation and logistical considerations. In addition, the collection ports may be placed in a variety of positions. For example, one or more such ports may be placed on the top wall of the device or, in embodiments wherein the vectoring extends around 180 degrees (described in greater detail below), on the back wall behind the exit of the jet.

In some embodiments, the blowing and suction flow rates may be the same or similar. In such embodiments, it may be convenient to provide a single high-pressure blower to supply both flows, as also demonstrated by FIG. 5. In the embodiment shown in FIG. 5, the suction path is joined with the blowing path, with the blower 115 positioned in between to provide for both the blowing flow 135 and the suction flow 145.

Although any apparatus available to one of skill in the art may be used, in one embodiment, a variable-speed ring compressor is provided as the "blower" to supply the suction/blowing force. Systems may also be designed to correlate the suction and blowing flow rates such that they are maintained at a particular percentage of the jet flow rate. This allows a user to easily vary the jet flow rate while maintaining the percentage of suction and blowing constant relative to the jet flow rate. Moreover, it should be apparent that embodiments of the invention provide for a highly scalable and inherently flexible system in many other regards, due in part to the number of adjustable inputs, including jet flow rate, jet vector angle, collector design, etc.

Through experimentation, it has been found that the vectoring angle increases linearly with the suction flow rate divided by the jet flow rate, independent of the jet velocity. Additionally, the vector angle can be held constant as the jet flow rate increases by also increasing the suction and blowing flow rate.

Figure 3:
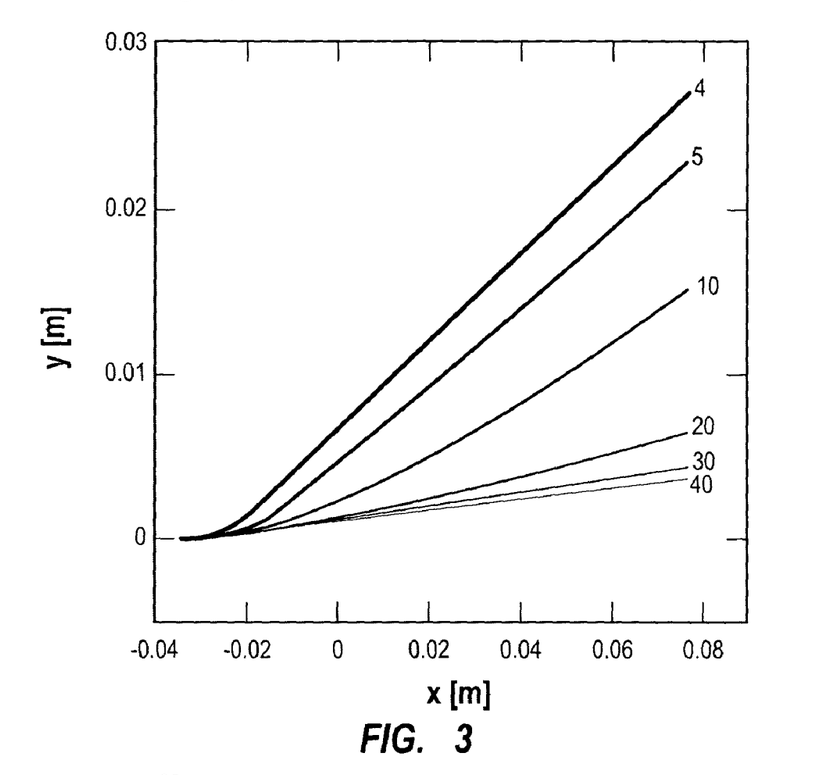
FIG. 3 is a graph showing the predicted trajectories of water droplets released upstream of the exit of fluid stream at the same location.
Figure 4:
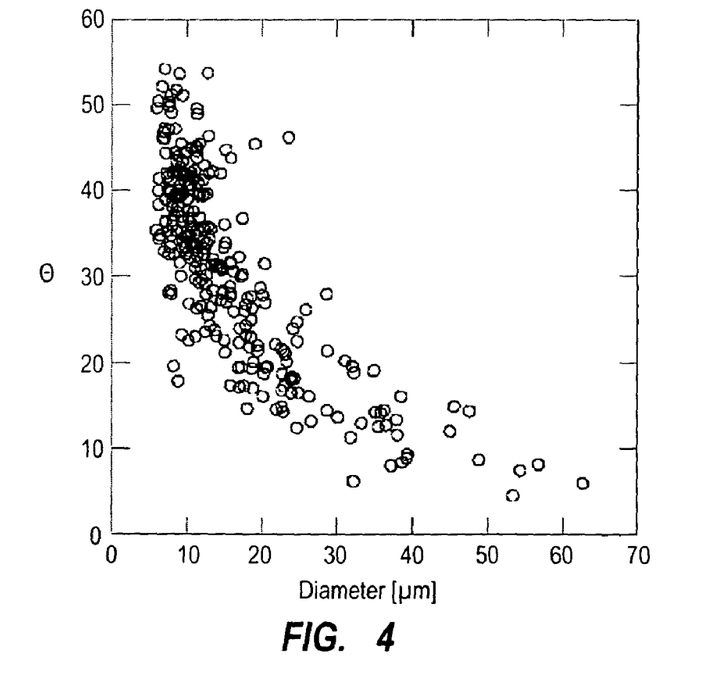
FIG. 4 is a graph showing experimentally measured trajectory angles ($\theta$) of water droplets as a function of droplet diameter (in $\mu$m).
Figure 6:
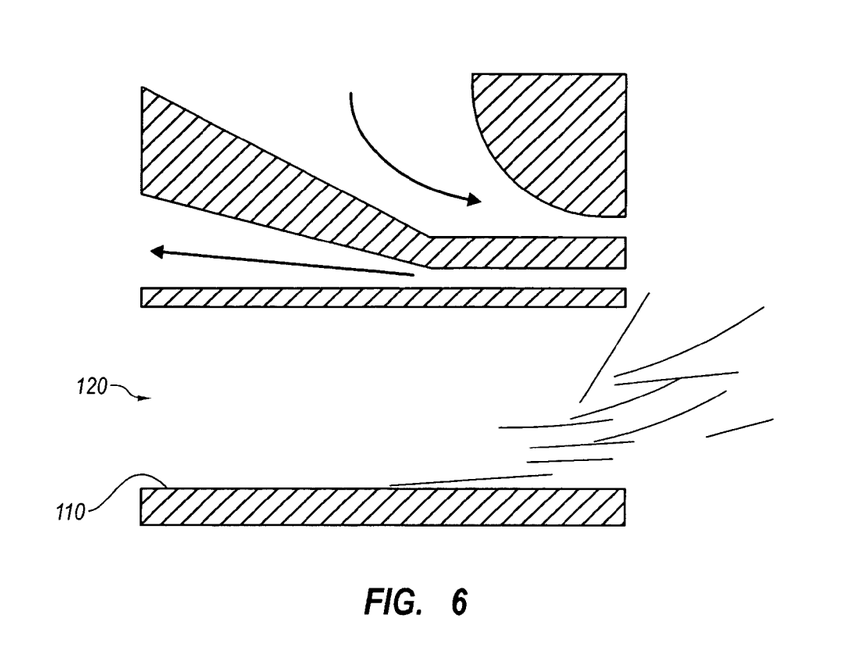
FIG. 6 represents one frame of a test video illustrating test results of fluidic vectoring using water droplets as test particles.

FIG. 6 illustrates test results using water droplets as test particles. A water mister nozzle was added to the aerodynamic jet vectoring jet setup upstream of the inlet to the channel 110 which directs the jet 120. Water droplets were generated with diameters in the range 10-100 μm (the particle size range was determined outside the vectoring facility). The droplets were visualized by illuminating them with a laser sheet and photographed with a high-speed camera. FIG. 6 represents one frame from the resultant video. It is clear that, while the jet is vectored uniformly, each particle has a unique trajectory due to its size. While these particles do not originate from the same location (resulting in the particle paths crossing and offset error in FIG. 6), their paths resemble the predicted trajectories shown in FIG. 3.

In the embodiments presented and discussed thus far, the exit of the blowing slot is parallel to the primary jet. However, other embodiments of the invention are contemplated in which this is not the case. It has been found that this orientation may limit the vector angle, since the jet flow is pushed downward to some extent by the blowing flow. This is evident in the pressure gradient field shown in FIG. 2. Regions 72, 62, and 74 just downstream and above the jet exit are pressure gradients generated when the blowing flow intersects the jet. Numerical simulations of aerodynamic vectoring using oscillatory blowing have shown that angling the slot upward may result in a substantially higher vector angle for the same suction and blowing flow rates. According to embodiments design for oscillatory blowing, a single exit port may be provided adjacent to the jet port. This single port may be configured to provide both a blowing and a suction flow. In such embodiments, the flow may oscillate or alternate back and forth from suction to blowing flows through the same port.

Figure 7:
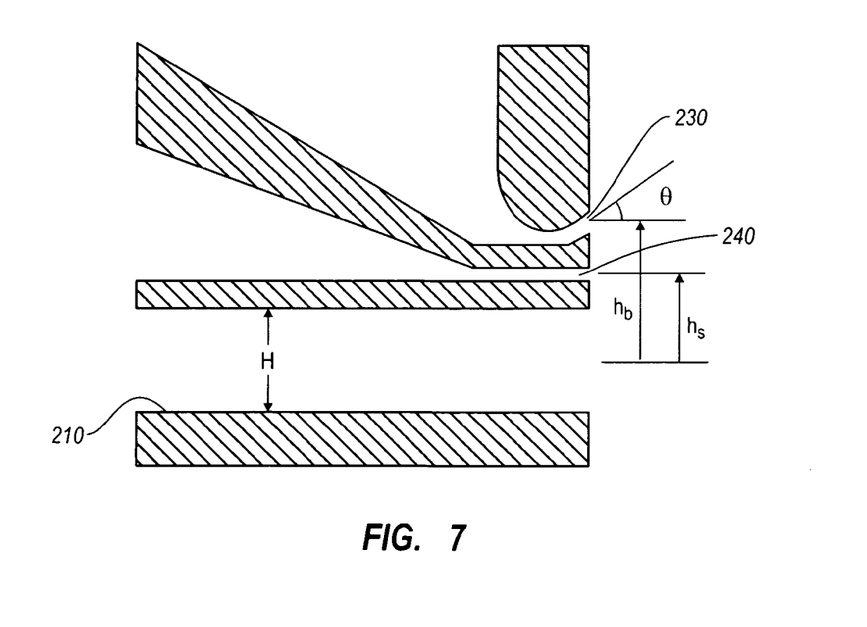
FIG. 7 is a cross-sectional view of still another embodiment of an apparatus for separating particles in a fluid stream.
Figure 8:
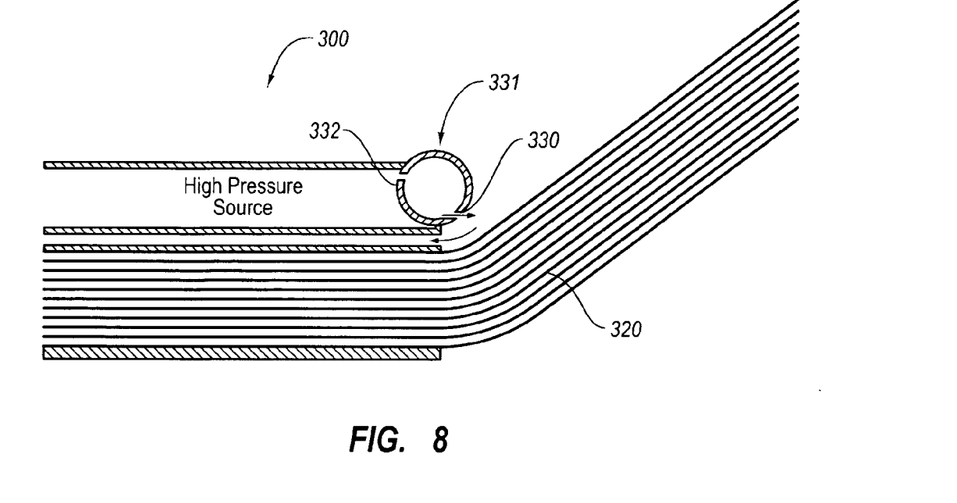
FIG. 8 is a cross-sectional view of yet another embodiment of an apparatus for separating particles in a fluid stream.
Figure 9:
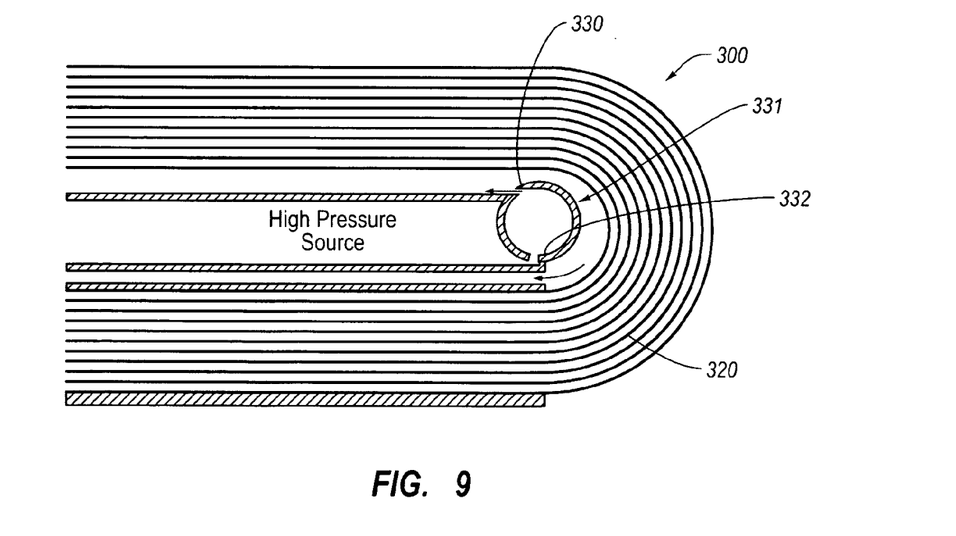
FIG. 9 is a cross-sectional view of the embodiment shown in FIG. 8, shown after a fluid stream has been redirected around 180 degrees.
Figure 10:
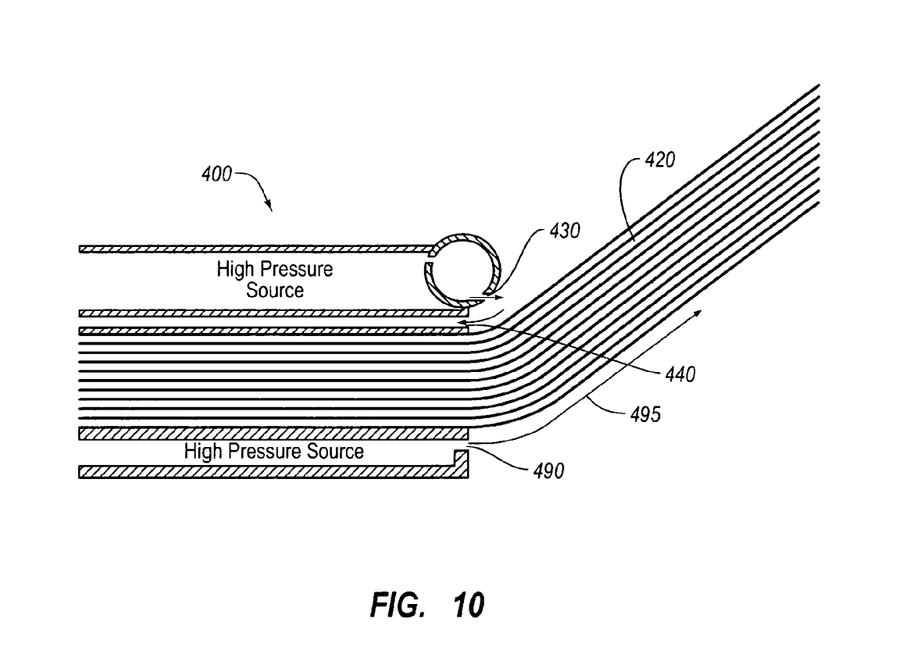
FIG. 10 is a cross-sectional view of another alternative embodiment of an apparatus for separating particles in a fluid stream.

Since a larger vector angle results in a wider range of sorting capability, the actuator may be modified with an angled blowing slot, as shown in FIG. 7. FIG. 7 illustrates an embodiment having a blowing port 230 that is angled away at angle θ from the direction at which the fluid stream travels through channel 210 prior to being redirected. Angle θ in this embodiment is also the angle at which blowing port 230 is angled relative to the orientation of suction port 240. Although in several of the simulations the angle θ was sixty degrees, this angle may vary tremendously depending on the parameters of the system and the desired outcome. In another simulation, the angle θ was twenty degrees. It was found that increasing the angle θ from zero to twenty degrees increased the resultant vectoring angle from about 22.5 to about 45 degrees (all else being equal).

Embodiments disclosed herein may be useful in a variety of fields, such as powder material processes, sample concentration, cell sorting, air quality monitoring, automotive exhaust distribution measurements, and blood cell sorting, for example. A number of optional features may also be added to improve the accuracy or other characteristics of the invention, such as surrounding the aerosol to be sorted with a "jacket" of clean air. This may result in a stream of particles that originate from a more narrow region. As another option, systems may be designed such that the jet width H (see FIG. 7) can easily be varied. Still other embodiments are contemplated in which the distance between the center of the channel 210 and the suction port 240, $h_s$, and/or the distance between the center of the channel 210 and the blowing port 230, $h_b$, vary or may be adjustable (see FIG. 7).

FIGS. 8 and 9 illustrate yet another alterative embodiment. Particle sorter 300 is similar to embodiments previously described, except that it includes an adjustable blowing port 330. In other words, the angle at which the blowing port 330 directs fluid relative to the fluid stream 320 is adjustable. In the depicted embodiment, the blowing port 330 comprises a slot 330 positioned on a rotatable cylinder 331 to thereby allow the angle at which the blowing port 330 directs fluid relative to the fluid stream 320 to be adjusted by rotating the cylinder 331. The cylinder 331 has a second slot 332 through which the blowing flow from the high pressure source may enter the cylinder 331.

Particle sorter 300 may be used to statically vary the blowing angle in between sorting sessions. Alternatively, particle sorter 300 may be rotated in the presence of a fluid stream 320 to redirect the fluid stream 320 around a larger angle than would otherwise be possible. It is thought that it may be possible to redirect the fluid stream 320 around 180 degrees, as shown in FIG. 9. It is thought that the low pressure area may be gradually wrapped all the way around the cylinder 331 by rotating the cylinder 331 and will eventually maintain itself in that manner to continually redirect the stream 320 around 180 degrees. This would allow for sorting of finer gradations of particle sizes to thereby achieve a finer sorting "signal".

Still another embodiment is shown in FIG. 10. Particle sorter 400 is similar to particle sorter 300 shown in FIGS. 8 and 9, except that it includes a second blowing port 490 directing a second blowing flow 495. It has been found that, under certain circumstances, instability may be created in the jet 420. In particular, it has been found that a vortex may sometimes be formed below the jet 420, thereby creating instability in the jet 420. To alleviate this problem, second blowing port 490 may be provided below jet 420. In the depicted embodiment, the second blowing port 490 is positioned adjacent to jet 420 such that the jet 420 is positioned in between the suction port 440 and the second blowing port 490. It is expected that the blowing flow 495 provided by second blowing port 490 below the jet 420 may help suppress instability in the jet 420.

Each of the channels described herein are examples means for directing a fluid stream. Each of the port configurations described herein, which operate to create a low pressure region, are examples of means for redirecting a fluid stream to separate particles in the fluid stream by size. Each of the collection port configurations described herein are examples of means for sorting particles in the fluid stream by size.

The above description fully discloses the invention including preferred embodiments thereof. Without further elaboration, it is believed that one skilled in the art can use the preceding description to utilize the invention to its fullest extent. Therefore the examples and embodiments disclosed herein are to be construed as merely illustrative and not a limitation of the scope of the present invention in any way.

It will be obvious to those having skill in the art that many changes may be made to the details of the above-described embodiments without departing from the underlying principles of the invention. The scope of the present invention should, therefore, be determined only by the following claims.

The invention claimed is:

1. An apparatus for separating particles in a fluid stream, comprising:
   a housing;
   a channel contained at least partially within the housing for the fluid stream;
   a suction channel terminating at a suction port, wherein the suction port is positioned adjacent to the fluid stream; and
   a blowing channel terminating at a blowing port, wherein the blowing port is positioned adjacent to the suction port such that the suction port is positioned in between the fluid stream and the blowing port, wherein the blowing port and the suction port are configured to create a low pressure region and thereby redirect the first fluid stream towards the low pressure region.

2. The apparatus of claim 1, further comprising:
   a blower positioned in fluid communication with the blowing channel and configured to provide a blowing stream out of the blowing port.

3. The apparatus of claim 2, wherein the blower is positioned in fluid communication with the suction channel and is configured to provide a suction stream into the suction port.

4. The apparatus of claim 1, further comprising:
   a plurality of collection ports positioned downstream of the location at which the fluid stream is redirected to sort particles in the fluid stream by size.

5. The apparatus of claim 4, further comprising:
   a plurality of collection bins corresponding to the plurality of collection ports to collect the sorted particles by size.

6. The apparatus of claim 1, further comprising:
   a second blowing channel terminating at a second blowing port, wherein the second blowing port is positioned adjacent to the fluid stream such that the fluid stream is positioned in between the suction port and the second blowing port.

7. The apparatus of claim 1, wherein the housing comprises a vent positioned adjacent to the fluid stream.

8. An apparatus for separating particles in a fluid stream, comprising:
   a housing;
   a channel contained at least partially within the housing for the fluid stream;
   a suction channel terminating at a suction port, wherein the suction port is positioned adjacent to the fluid stream;
   a blowing channel terminating at a blowing port, wherein the blowing port is positioned adjacent to the suction port such that the suction port is positioned in between the fluid stream and the blowing port, wherein the blowing port and the suction port are configured to create a low pressure region and thereby redirect the first fluid stream towards the low, pressure region;
   a blower positioned in fluid communication with the blowing channel and configured to provide a blowing stream out of the blowing port, wherein the blower is also positioned in fluid communication with the suction channel and is further configured to provide a suction stream into the suction port; and
   a plurality of collection ports positioned downstream of the location at which the fluid stream is redirected to sort particles in the fluid stream by size.

* * * * *